United States Patent [19]

Badoz et al.

[11] 4,299,494
[45] Nov. 10, 1981

[54] MEASUREMENT OF HEAT TRANSFER BETWEEN A SPECIMEN AND AN AMBIENT MEDIUM

[75] Inventors: Jacques Badoz; Albert Boccara; Danièle Fournier born Juillard, all of Paris, France

[73] Assignee: Agence Nationale de Valorisation de la Recherche (ANVAR), Neuilly sur Seine, France

[21] Appl. No.: 151,761

[22] Filed: May 21, 1980

[30] Foreign Application Priority Data

May 22, 1979 [FR] France .................. 79 12985

[51] Int. Cl.³ .................................. G01N 21/00
[52] U.S. Cl. .......................... 356/432; 356/128
[58] Field of Search .................. 356/432–442, 356/128, 130, 43, 129, 131–137; 73/190 EW

[56] References Cited

U.S. PATENT DOCUMENTS

| 3,566,385 | 2/1971 | Lawson | 356/128 |
| 3,948,345 | 4/1976 | Rosencwaig | 73/579 |
| 4,213,699 | 7/1980 | Moore | 356/70 |

OTHER PUBLICATIONS

Herrmann, W. et al., "Trace Analysis in Gases by Laser-Induced Schlieren Technique", IBM Technical Disclosure Bull., vol. 21, No. 10, p. 4209, Mar. 1979.
Hordvik, A., "Measurement Techniques for Small Absorption Coefficients: Recent Advances", pp. 2827–2833, Applied Optic, vol. 16, No. 11, Nov. 1977.
Sakakibara, T. et al., "Instantaneous Measurement of Spatial Temperature Distribution Through Light Beams Deflection Method", pp. 40–42, *Journal of Physics E: Scientific Instruments,* vol. 16, No. 1, Jan. 1973.
Friend, A. L. et al., "Improved Method for the Optical Determination of Temperature Profiles", Boundary-Layer Meteorology, pp. 227–239, 1970.

*Primary Examiner*—John K. Corbin
*Assistant Examiner*—Bruce Y. Arnold
*Attorney, Agent, or Firm*—John T. Synnestvedt; Albert L. Free

[57] ABSTRACT

The method comprises measuring the heat transfer between a specimen of the substance in condensed phase and an ambient gas. The heat transfer is detected by measurement of the amplitude of the angular movement of a pencil of light which is directed substantially parallel to the surface of the specimen subjected to energization variable in time, and which passes through an area located close to said surface. The device comprises a specimen support and a monochromator.

15 Claims, 7 Drawing Figures

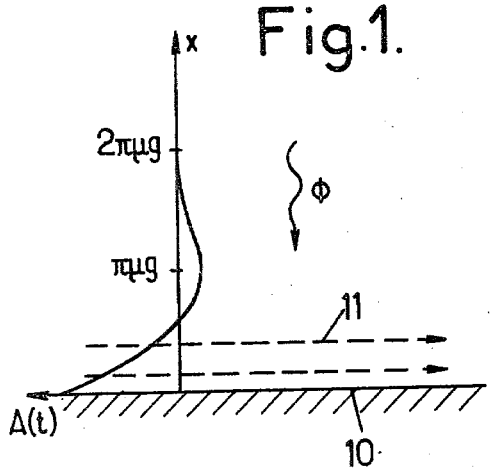
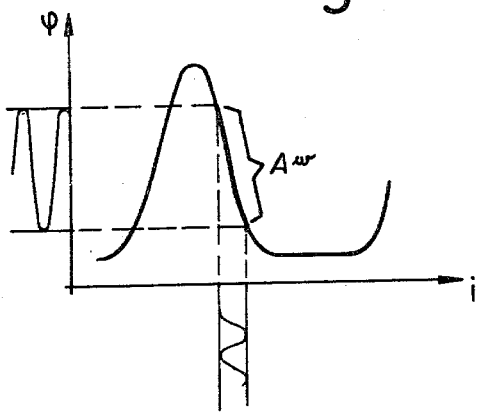
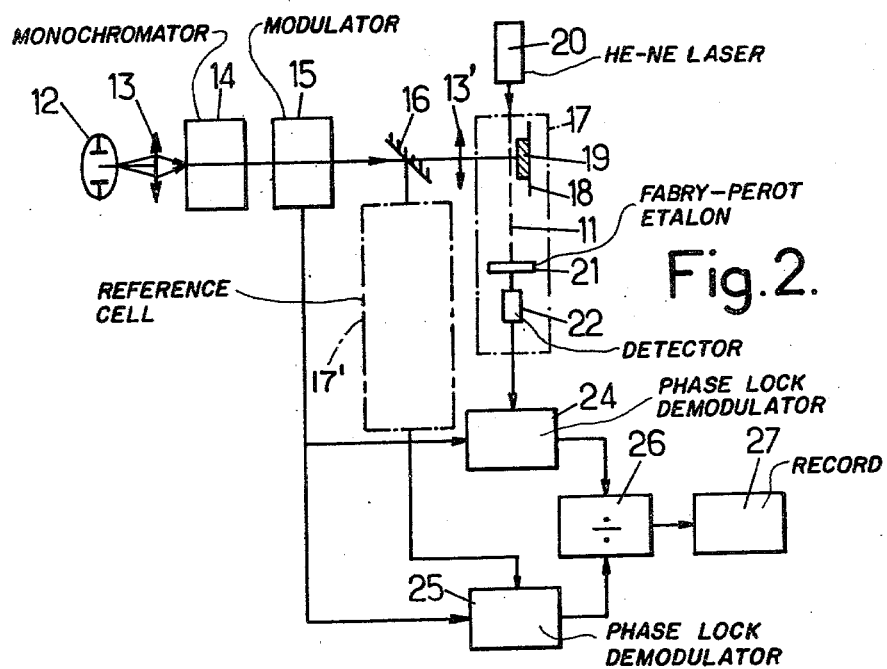
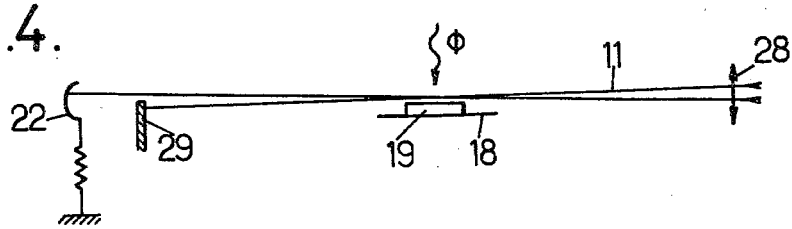

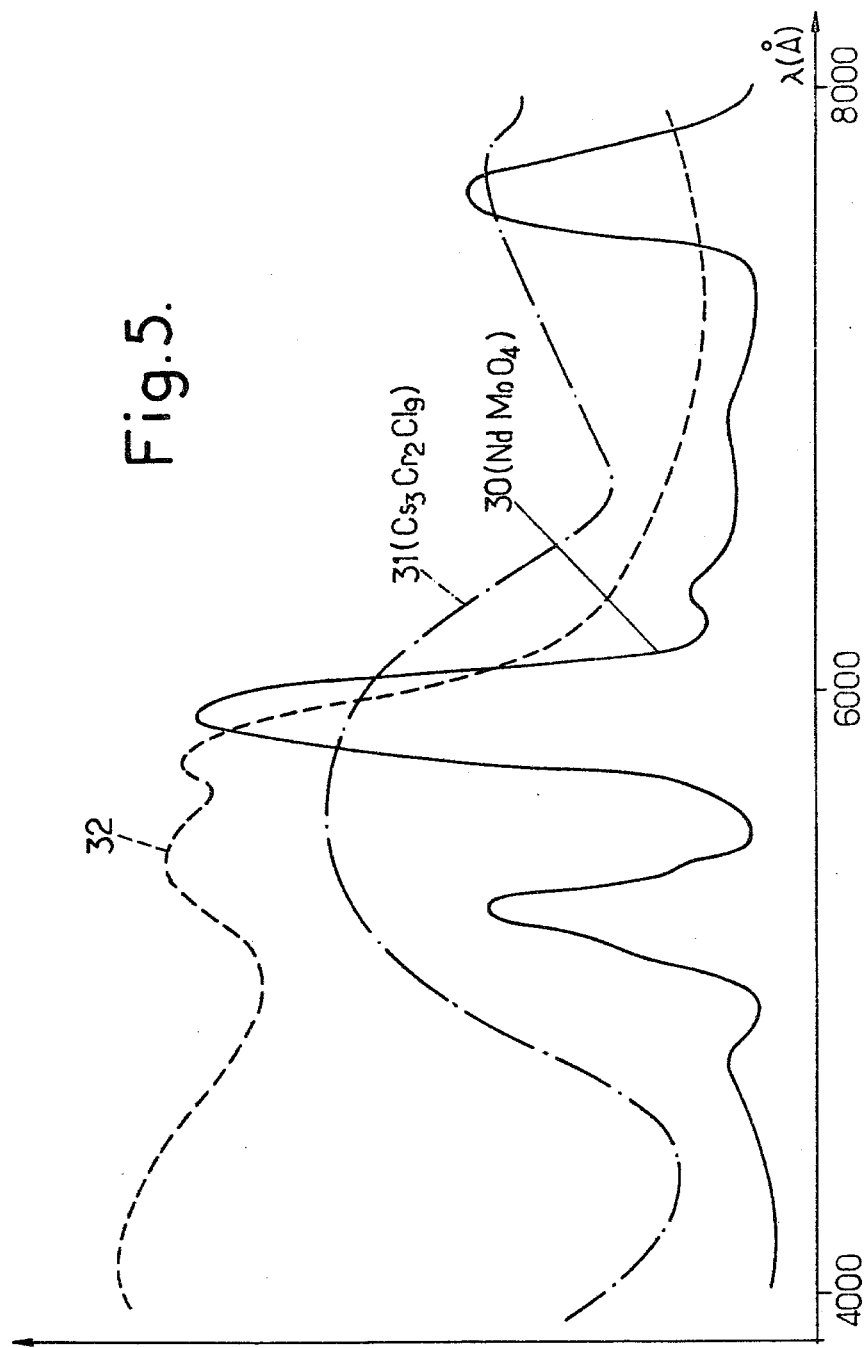

MEASUREMENT OF HEAT TRANSFER BETWEEN A SPECIMEN AND AN AMBIENT MEDIUM

BACKGROUND AND SUMMARY OF THE INVENTION

The invention relates to methods and devices for measuring heat transfer between a specimen or sample of condensed matter and an ambient gas, suitable for use in analysis of that matter; a particularly important application of the method and device consists in the measurement of the light energy absorption spectrum of the specimen.

For several years, there has been an important development in spectroscopy using the conversion into heat of light energy received by the specimen and heat transfer between one surface of the specimen and a gas medium contacting the surface. Such spectrometry techniques can be used in cases where conventional absorption spectroscopy is not suitable, notably in the case of very absorbent, diffusing, solid or semisolid substances.

Prior art techniques of that type consist in directing a monochromatic light flux of varying magnitude onto the specimen located in a gas and detecting the heat transfer between the surface receiving the flux and the ambient gas. Photoacoustic spectroscopy, described in U.S. Pat. No. 3,948,345 (Rosencwaig), uses conversion of heat energy into acoustic energy. A probe (for example a microphone) placed in the vicinity of the specimen supplies electrical signals at the modulation frequency.

Photo-acoustic spectroscopy has drawbacks: the measuring system is very sensitive to mechanical vibration; it requires the use of a measuring cell with thick windows which have an unfavorable effect on the accuracy of the measurements; the size of the samples is obviously limited to that of the cell, generally of small size (typically $3 \times 3 \times 8$ mm$^3$). Lastly, the probe and the walls of the cell are subject to interference effects.

It is an object of the present invention to remove the above mentioned shortcomings; it is a more particular object to provide a method and a device which have a low sensitivity to external disturbances, while they offer a signal/noise ratio at least signal to the techniques of photo-acoustic spectroscopy and do not impose excessive limitations on the size of the specimens.

According to a feature of the invention there is provided a method for measuring heat transfer between a specimen of a substance in condensed phase and an ambient gas, characterised in that the transfers are detected by measuring the amplitude of the angular displacement of a light pencil which is directed substantially parallel to the surface of the specimen, subject to an energisation whose amplitude varies in time, and which passes through a zone situated in the proximity of said surface.

When the absorption coefficient of the specimen is to be measured, the specimen is energized by a light flux whose magnitude varies with time, advantageously periodically.

In all cases, the light pencil must pass through a zone wherein an appreciable refractive gradient exists, hence very close to the surface. The pencil of light is not necessarily a collimated beam in the form of a right cylinder, but it has sufficiently well-defined boundaries to enable detection of the changes in its angular orientation.

According to another aspect of the invention there is provided a measuring device which comprises a specimen support, means for directing a light pencil parallel to said surface and in the immediate proximity of said specimen and means for detecting the amplitude of the angular displacement of the light pencil.

The energizing light beam is advantageously made monochromatic. By causing the wavelength of the light flux to vary, a variation curve of the deviation as a function of the wavelength, characteristic of the material will be obtained.

However, it is also possible to code the energizing light flux, for example by means of an interferometer with Fourier transform or selective modulation.

This invention will be better understood from the following description of devices which constitute particular embodiments thereof, given by way of nonlimiting examples, and of the method that they utilise.

SHORT DESCRIPTION OF THE DRAWINGS

The description refers to the accompanying drawings, in which:

FIG. 1 is a schematic diagram showing the variation in amplitude of the alternating component of the variation in temperature, along a line perpendicular to a surface which receives a modulation light flux;

FIG. 2 is a block diagram of an apparatus constituing a first embodiment of a device according to the invention;

FIG. 3 shows a curve representing the light flux transmitted by the Fabry-Perot etalon of the device of FIG. 2;

FIG. 4 is a schematic diagram showing in detail a device constituting a modification of the embodiment of FIG. 2;

FIG. 5 shows, by way of example, the spectra obtained with three distinct materials.

DESCRIPTION OF PARTICULAR EMBODIMENTS

Figure 6:
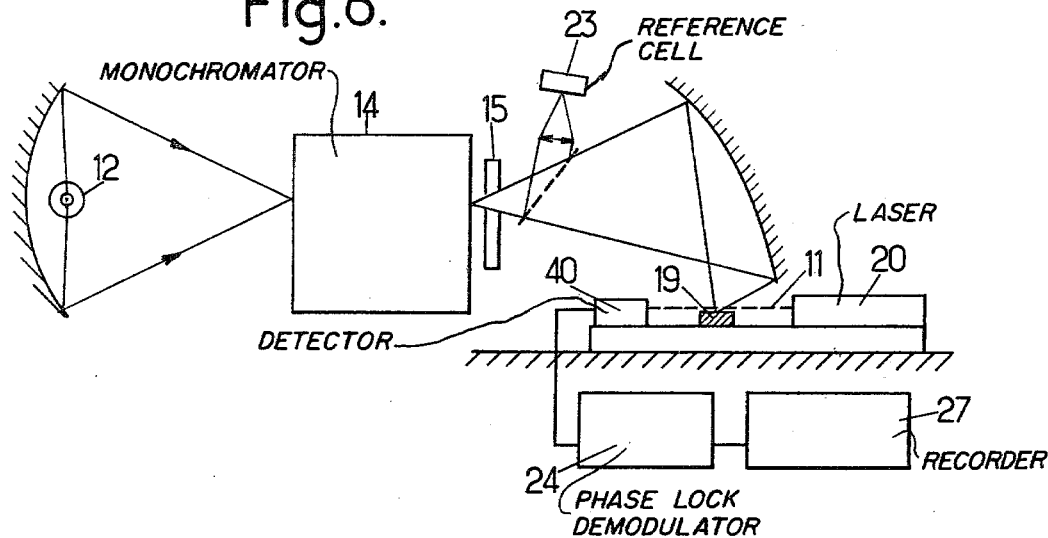
FIGS. 6 and 7 are diagrams showing two other embodiments.

Before describing an embodiment according to the invention, the physical phenomena utilized by the invention and which are related to the mirage effect will first be explained with reference to FIG. 1.

When the flat surface 10 of a specimen is irradiated by a modulated light flux $\Phi$, this surface heats up periodically, at least if the de-energisation process is principally non-radiating, as is assumed below. The rise in temperature of the surface is directly connected with the absorption coefficient of the specimen and the gas (generally air) in contact with the surface 10 experiences a modification in its temperature periodically within a zone of finite thickness. The variation in amplitude of the alternating component A(t) as a function of the distance x to the surface 10, has the shape shown diagrammatically in FIG. 1. The curve may be characterised by the length of thermal diffusion, $\mu g$:

$$\mu g = \sqrt{\frac{2k}{\omega \rho C_p}}$$

In this formula, the parameters have the following connotations:
k thermal conductivity
$C_p$ specific heat ρ density ω = 2πf (f: modulation frequency of the flux Φ).

For air, at a frequency of 100 Hz, the length of thermal diffusion $\mu_g$ is of the order of a millimeter.

It is seen that a temperature gradient dT/dx appears close to the surface 10 and is manifested by a gradient of index dn/dx.

According to the invention, a light pencil or beam 11 is passed through this zone, indicated in dashed lines in FIG. 1. The thermal gradient causes a periodic angular deflection of the axis of the beam: the amplitude of the thermal gradient being proportional to the heating of the surface, the amplitude of the angular displacement provides a measurement of the periodic component of the temperature at the surface of the specimen.

FIG. 2 shows a device constituting a particular embodiment of the invention.

This device includes a light source 12, for example, a xenon lamp. An optical system 13, shown diagrammatically by a single lens, receives the light coming from the lamp 12 and focusses the beam emitted onto the input of a monochromator 14 of conventional type, providing a light beam located entirely within a narrow frequency band, but adjustable by actuation of the monochromator.

A modulator 15, which may in the majority of cases be constituted by a chopper, modulates the light beam at the predetermined frequency f. An optical system 13' focusses the beam onto the specimen 19.

The device shown in FIG. 2 carries out relative measurements with respect to a standard substance. For this purpose, it includes, at the output of the modulator 15, a beam separator 16, constituted for example by a semi-reflecting mirror.

The transmitted portion of the beam arrives at the measuring cell 17 in which a support 18 is provided to receive a specimen 19. The invention applies to any specimen of a substance in condensed phase (solid, liquid, gel, powder, crystals, etc.) and it will be noted that, the effect used for the detection being independent of the surface condition, the field of application is very wide. In FIG. 2, the support 18 is vertical. In certain cases, it will be, on the other hand, indispensible to place it horizontally, to retain a liquid specimen for example.

The light pencil 11 whose deviation is measured is emitted by a low power source supplying a monochromatic radiation, for example a helium-neon laser 20. A power of 1 mW will generally be satisfactory. The pencil 11 skirts the irradiated surface of the specimen 19 and then passes through a unit 21 which modifies the amplitude of the beam in a ratio which depends on the incidence i of the beam. This unit 21 is, for example, a Fabry-Perot etalon which is placed, not perpendicularly to the pencil emerging from the source 20, but at an angle selected so that the response relationship is substantially linear. In FIG. 3 is shown the variation of the transmitted flux $\phi$ as a function of the incidence i and the selected operating area (in dash lines).

The working area, indicated by bracket Aw, must cover the angular divergence of the laser, of the order of a milli-radian.

The flux which has passed through the standard 21 is collected by a detector, which may be a PIN diode 22.

The beam reflected by the separator 16 is received by a reference cell 17' similar to the cell 17, but of which the specimen is constituted by a material of well defined characteristics similar to a black body. Carbon black may notably be used or gold black.

The output signal coming from the detector 22 is applied, if necessary after amplification, to a synchronous demodulator 24 which supplies, at its output, a continuous signal representing the light absorption by the specimen 19 for the wave length of the beam of magnitude Φ. The demodulation reference signal can come from the modulator 15. Similarly, the output signal coming from the detector of the reference cell 17' is applied to a synchronous demodulator 25, if necessary after amplification. Signals coming from the demodulators 24 and 25 are applied to an analog divider circuit 26 of which the output is applied to a recorder 27. The processing may naturally also be carried out digitally.

The device shown in FIG. 2 has enabled a measurement of deflection values of the pencil 11 of $10^{-9}$ radian, by operating at modulation frequencies of some tens of Hertz. If the modulation frequency f is further increased, the thermal diffusion length $\mu_g$ diminishes, since it is a function of $\omega^{-\frac{1}{2}}$. It may then be necessary to focus the light pencil so that its thickness is sufficiently small where it skims the specimen. FIG. 4 (wherein the members corresponding to those of FIG. 2 bear the same reference numeral) shows an arrangement which can then be used. The divergence of the beam 11 delivered by lens 28 is then such that there is no drawback to detecting the angle of rotation of the beam at a finite distance, and not on a cylindrical beam as in the case of FIG. 2. In the path of the beam 11 is placed a plate 29 forming a diaphragm (razor blade, for example) which replaces the standard 21 of FIG. 2. The detector 22 may be placed immediately behind plate 29. The loss of sensitivity due to the increase in the divergence of the beam is more than compensated due to the fact that the beam 11 passes entirely through the zone very close to the surface of the specimen 19, in which zone the gradient is a maximum.

Calculation shows that, if the smallest detectable angle of deflection is of the order of $10^{-9}$ radians, it is possible to establish temperature gradients dT/dx as small as $0.2 \times 10^{-3}$/mm by using as a gas air whose refractivity index is substantially equal to 1 and dn/dt is of the order of $10^{-6}$.

The signal/noise ratio obtained is of the order of $5 \times 10^{+3}$ in the case of a specimen of carbon black for a modulated flux of about 10 mW at the output of the monochromator, that is to say, of the same order of magnitude as in the case of photo-acoustic spectroscopy.

By way of example, FIG. 5 shows the spectra obtained from specimens in various phases. Curve 30 corresponds to a crystal of Nd Mo O$_4$, curve 31 to Cs$_3$ Cr$_2$ Cl$_9$ powder and curve 32 to a specimen of fresh blood.

The device according to the invention is capable of numerous modifications and numerous additions, in particular to improve the signal/noise ratio by reducing the noise of the laser used as a light probe. In particular, whereas in the embodiment described the energizing light flux is monochromatic, it is also possible to energize the specimen by a coded polychromatic flux, such as that produced by a Fourier transform spectrometer or by a selective modulation spectrometer. The detection of the heat transfers will then be carrier out as indicated above and the result of this measurement can be processed in known manner, according to the type of coding selected, to obtain the contribution of each wave length to the heat transfers detected.

In the same way, the method and the device according to the invention enable the measurement of heat transfers generated by light pulses rather than by a light whose amplitude is modulated according to an approximately sine law. Finally, the detection of the angular movement of the beam can be done by any suitable means. There exist detectors enabling the measurement with great accuracy of the position of a light spot. By way of example, may be mentioned photo-diode strips. Such detectors placed in the image plane of an optical system enable the measurement of the angular displacement of the flux received by this system and can thus be advantageously used for the practising of the invention.

FIG. 6, wherein the members corresponding to those shown in FIG. 2 are denoted by the same reference numeral, shows a modification of the device which may not include a reference measuring cell and also it permits the measurement of the absorption spectrum (that is to say the variation in the absorption coefficient as a function of the wave length of the absorbed radiation) of the specimen 19, in the range going from 2000 Å to about 2800 Å. The light flux of a source 12, constituted by a xenon arc of 450 W, passes through an adjustable monochromator 14 open to f/2. After modulation by a rotary disk 15, it is focussed by an elliptical mirror on to the specimen. The monochromatic beam 11 of an He-Ne 2o laser of 1 mW is focussed in the thermal gradient zone and the periodic deflection of the beam 11 is measured by means of a detector 40 which may be one of those referred to above, a photo-electric cell or a cell with two quadrants of the type marketed by Silicon Detector Corporation.

If it is considered necessary to carry out differential measurements to be clear of instabilities of the source, it suffices to add to the assembly a semitransparent plate for reflecting a fraction of the beam of the arc to a reference beam detector 23 constituted for example by a photoacoustic cell or a pyroelectric detector.

It has been found that the signal equivalent to the noise of such an assembly is very weak and corresponds to rises of temperature of about $10^{-4°}$ C. at the surface of the specimen.

It must again be noted that the stability in the position of the pencil 11 is not critical: a variation of the order of 1/10 of the position of the pencil with respect to the surface is generally perfectly tolerable, which renders the method useful outside of the laboratory.

Figure 7:
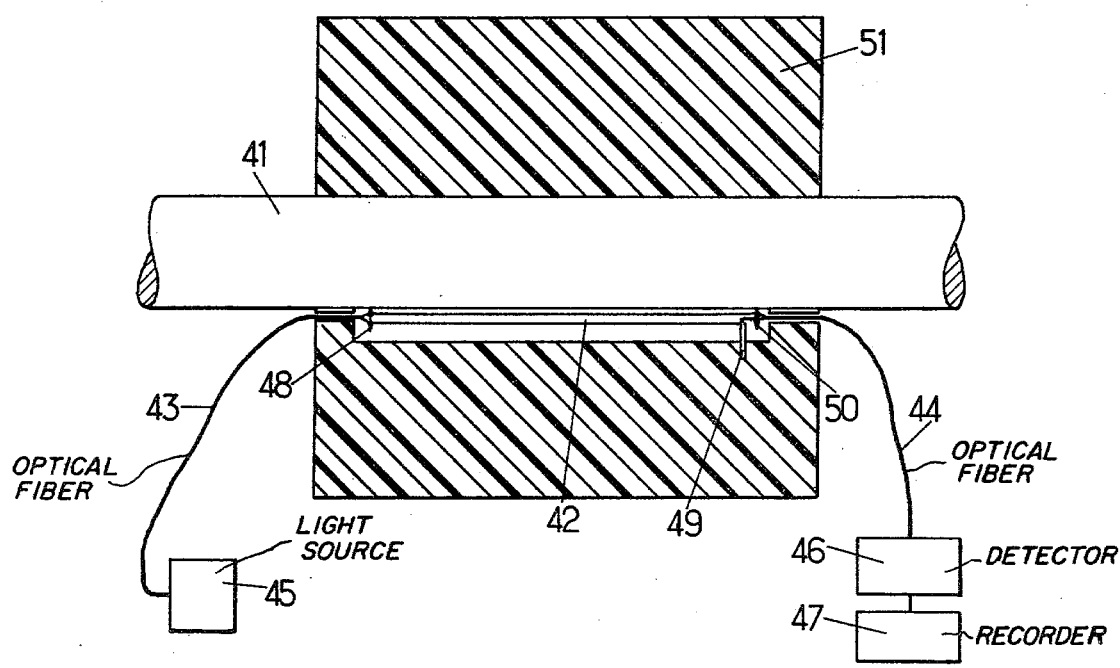

The method is also useful to determine the periodic heating of a solid having another origin than irradiation, for exampe an internal release. FIG. 7 shows, by way of example, a measuring device for the value of the alternating current in a high voltage line 41. The light beam 42 for measuring the thermal gradient is then directed parallel to the cable on a rectilinear section of the latter. To locate far away from the cable the members traversed by the electrical signals, the device comprises optical fibers 43 and 44 for introducing light from the source 45 (He-Ne laser for example) and returning light to the detector 46 associated with a recorder 47.

An optical system 28 placed at the output of the fiber 43 forms the light pencil 42. A plate 49 placed so as to intercept one half of the undeflected pencil and an optical system enable a flux which is a function of the deflection to be received by detector 46.

All of the elements of the device whose position must remain invariable with respect to cable 41 can be housed in an insulating sleeve 51 for protection against atmospheric agents.

In practice, it is possible to use a zone of interaction of the pencil of the order of 10 cm. The intensity which passes through the cable 41 can be deduced from the deviation either by calibration, or by calculation of the losses in the cable.

A similar device can be constructed each time that it is desired to determine the periodic component of heat release within a specimen or sample.

We claim:

1. Method for measuring heat transfer between a specimen of condensed matter and an ambient gas, comprising directing a pencil of light substantially parallel and close to a surface of the specimen in contact with gas while said specimen is subjected to energisation variable in time at a predetermined frequency; and measuring the magnitude of the angular alternating deflection movement of said light pencil.

2. Method according to claim 1 for measuring the absorption coefficient of said specimen, wherein said subjection to energization comprises directing a light flux whose magnitude varies in time onto said surface of said specimen.

3. Device for measuring heat transfer between a specimen of condensed matter which is subjected to periodical energization at a predetermined frequency; and an ambient gas, comprising a support for receiving a specimen, means for directing a pencil of light parallel to a straight line in a surface of the specimen in contact with ambient gas and in immediate proximity to said surface, and means for detecting the magnitude of the angular deflection oscillaton of the pencil of light.

4. Device according to claim 3 for measuring the light absorption coefficient of said specimen, wherein said periodical energization is provided by means for directing an energising light flux variable in time onto said surface of the specimen.

5. Device according to claim 3 or 4, wherein said pencil of light is substantially cylindrical and wherein the detector means comprise a Fabry-Perot etalon positioned at an angle with respect to said pencil of light and a detector located to receive the light at the output of the Fabry-Perot etalon.

6. Device according to claim 3, wherein the pencil of light is a convergent pencil focused in the immediate proximity of said surface of the specimen.

7. Device according to claim 6, wherein the detector means comprises a blade located to partly intercept said pencil and a detector positioned behind the plate in the direction of said pencil.

8. Device according to claim 3 for measuring the temperature variations of the specimen while it is traversed by an alternating electric current, further comprising respective light guides for leading the pencil of light from a source and collecting it for transmission to said detecting means.

9. Device according to claim 8, wherein said light guides are optical fibers.

10. Method for measuring the absorption spectrum of a specimen comprising directing a pencil of light substantially parallel and close to a surface of the specimen in contact with a gas while submitting said surface of the specimen to a flux of monochromatic light whose intensity is varied in time; varying the wavelength of said flux; and, measuring the corresponding variations in the amount of deflection of said pencil so as to determine the absorption spectrum of the specimen.

11. Device for measuring the light absorption coefficient of a specimen of condensed matter comprising: a support for receiving a specimen; means for directing a pencil of light parallel and close to a surface of said specimen in contact with ambient gas; means for directing a flux of energizing monochromatic light variable in time onto said surface of the specimen: and, means for detecting the magnitude of the angular deflection of the pencil of light.

12. Device according to claim 11, wherein said means for directing a flux of energizing monochromatic light comprise means for adjustment of the wavelength of said monochromatic flux at a variable value.

13. Device according to claim 11, further comprising means for coding the energising light flux.

14. Device according to claim 13, wherein the means for coding the energising light flux include a Fourier transform interferometer or a selective modulation interferometer.

15. Device according to claim 4 or 11, further comprising: means for splitting the energizing light flux into two beams, one of which is applied to the specimen and the other to a reference standard; and, an additional detector operatively associated with the reference standard, wherein the detector associated with the specimen and the detector associated with the standard are connected to deliver electric output signals to respective inputs of a divider circuit.

* * * * *